United States Patent
Dove et al.

(10) Patent No.: US 10,258,952 B2
(45) Date of Patent: Apr. 16, 2019

(54) METHOD FOR INCREASING GAS COMPONENTS IN A FLUID

(71) Applicants: Larry John Dove, Edmonton (CA); James Von Krosigk, Buchanan Dam, TX (US)

(72) Inventors: Larry John Dove, Edmonton (CA); James Von Krosigk, Buchanan Dam, TX (US)

(*) Notice: Subject to any disclaimer, the term of this patent is extended or adjusted under 35 U.S.C. 154(b) by 119 days.

(21) Appl. No.: 15/476,159

(22) Filed: Mar. 31, 2017

(65) Prior Publication Data

US 2018/0280915 A1 Oct. 4, 2018

(51) Int. Cl.
*B01J 19/00* (2006.01)
*B01D 17/04* (2006.01)
(Continued)

(52) U.S. Cl.
CPC ........ *B01J 19/0006* (2013.01); *B01D 17/047* (2013.01); *B01D 17/12* (2013.01);
(Continued)

(58) Field of Classification Search
CPC .............. B01J 19/087; B01J 19/0006; B01J 2219/0877; B01J 2219/00164; C10M 173/02; C10M 113/02; C10M 2201/041; C10M 2201/02; B01F 15/00162; B01F 15/00136; B01F 3/04978; B01F 5/0057;
(Continued)

(56) References Cited

U.S. PATENT DOCUMENTS 4,214,962 A * 7/1980 Pincon ...................... A61L 2/08
204/157.44
4,659,479 A * 4/1987 Stickler ................... C02F 1/485
210/222
(Continued)

OTHER PUBLICATIONS

"Pressure sensor" Wikipedia published Feb. 16, 2014 accessed at <https://en.wikipedia.org/w/index.php?title=Pressure_sensor&oldid=595691755> (Year: 2014).*
(Continued)

*Primary Examiner* — Amber R Orlando
*Assistant Examiner* — Stephen Hobson
(74) *Attorney, Agent, or Firm* — Buskop Law Group, P.C.; Wendy Buskop

(57) ABSTRACT

An apparatus for increasing gas components in a fluid uses a controller connected to a network and client device for remote control of fluid flow rates, magnet field intensity, and pressure of fluid based on preset parameters. Conductive wire coiled around a magnet fluid treatment device generates a bidirectional magnetic flux to magnetically treat fluid in the conduit at an entry pressure. A variable frequency generator energizes the wire creating magnetic flux lines to pass through the fluid flow conduit. A gas injector receives fluid at the gas injector entry pressure and lowers the gas injector entry pressure of the fluid to a gas injector discharge pressure. A treatment chamber receives the fluid at a treatment chamber entry pressure and lowers the treatment chamber entry pressure to a treatment chamber discharge pressure. The apparatus causes absorption of increased gas component into the fluid by from 10% to at least 500%.

10 Claims, 10 Drawing Sheets

(51) Int. Cl.
*B01D 17/12* (2006.01)
*C02F 1/44* (2006.01)
*B01D 61/10* (2006.01)
*C02F 3/12* (2006.01)
*C12M 1/00* (2006.01)
*C12M 1/36* (2006.01)
*C10L 10/02* (2006.01)
*C04B 40/00* (2006.01)
*B01J 19/08* (2006.01)
*B01F 5/04* (2006.01)
*B01F 5/00* (2006.01)
*B01F 3/04* (2006.01)
*C02F 1/00* (2006.01)
*C02F 1/48* (2006.01)
*B01D 53/78* (2006.01)
*B01D 53/60* (2006.01)
*B01F 15/00* (2006.01)
*C10M 173/02* (2006.01)
*C10M 113/02* (2006.01)
*B01D 53/18* (2006.01)
*C02F 103/08* (2006.01)
*C02F 1/76* (2006.01)

(52) U.S. Cl.
CPC ............ *B01D 53/18* (2013.01); *B01D 53/60* (2013.01); *B01D 53/78* (2013.01); *B01D 61/10* (2013.01); *B01F 3/0446* (2013.01); *B01F 3/04978* (2013.01); *B01F 5/0057* (2013.01); *B01F 5/0415* (2013.01); *B01F 15/00136* (2013.01); *B01F 15/00162* (2013.01); *B01J 19/087* (2013.01); *C02F 1/008* (2013.01); *C02F 1/441* (2013.01); *C02F 1/487* (2013.01); *C02F 3/1278* (2013.01); *C04B 40/0007* (2013.01); *C10L 10/02* (2013.01); *C10M 113/02* (2013.01); *C10M 173/02* (2013.01); *C12M 29/00* (2013.01); *C12M 41/48* (2013.01); *B01D 2259/814* (2013.01); *B01D 2311/2665* (2013.01); *B01F 2215/0014* (2013.01); *B01F 2215/0052* (2013.01); *B01F 2215/0073* (2013.01); *B01F 2215/0085* (2013.01); *B01J 2219/00162* (2013.01); *B01J 2219/00164* (2013.01); *B01J 2219/0854* (2013.01); *B01J 2219/0877* (2013.01); *C02F 1/481* (2013.01); *C02F 1/484* (2013.01); *C02F 1/76* (2013.01); *C02F 3/1294* (2013.01); *C02F 2103/08* (2013.01); *C02F 2201/486* (2013.01); *C02F 2209/005* (2013.01); *C02F 2209/03* (2013.01); *C02F 2209/40* (2013.01); *C02F 2301/026* (2013.01); *C10L 2230/22* (2013.01); *C10L 2290/14* (2013.01); *C10M 2201/02* (2013.01); *C10M 2201/041* (2013.01); *C10N 2250/141* (2013.01); *Y02W 10/15* (2015.05)

(58) Field of Classification Search
CPC ................. B01F 5/0415; B01F 3/0446; B01F 2215/0085; B01F 2215/0052; B01F 2215/0073; C02F 1/487; C02F 3/1278; C02F 1/008; C02F 1/441; C02F 2209/005; C02F 3/1294; C02F 2301/026; C02F 2209/03; C02F 1/76; C02F 2209/40; C02F 1/481; C02F 1/484; B01D 17/12; B01D 17/047; B01D 61/10; B01D 53/60; B01D 53/78; C10L 10/02; C10L 2290/14; C10L 2230/22; C04B 40/0007; C12M 41/48; C12M 29/00; C10N 2250/141

See application file for complete search history.

(56) References Cited

U.S. PATENT DOCUMENTS

| | | | | |
|---|---|---|---|---|
| 4,755,288 A * | 7/1988 | Mitchell | ................. | C02F 1/482 123/538 |
| 4,865,747 A * | 9/1989 | Larson | ................... | C02F 1/487 210/695 |
| 4,956,083 A * | 9/1990 | Tovar | ..................... | C02F 1/485 210/222 |
| 5,074,998 A * | 12/1991 | De Baat Doelman | .. | C02F 1/485 210/222 |
| 5,326,446 A * | 7/1994 | Binger | ................... | C02F 1/487 204/663 |
| 5,667,677 A * | 9/1997 | Stefanini | ................. | B01J 19/12 210/222 |
| 5,725,778 A * | 3/1998 | Cho | ........................ | C02F 1/485 210/222 |
| 6,145,542 A * | 11/2000 | Walker | .................... | C02F 1/48 123/538 |
| 6,193,878 B1 * | 2/2001 | Morse | ................. | B01J 19/0006 204/661 |
| 6,875,360 B2 * | 4/2005 | Allen | ..................... | C02F 1/487 204/554 |
| 7,048,786 B1 * | 5/2006 | Von Krosigk | ............ | C02F 1/34 210/150 |
| 7,137,621 B1 * | 11/2006 | Bagley | .................. | B01F 3/0446 261/79.2 |
| 7,238,289 B2 * | 7/2007 | Suddath | ................... | A23L 3/32 210/198.1 |
| 7,270,314 B1 * | 9/2007 | Von Krosigk | .......... | C02F 1/005 210/748.01 |
| 7,288,185 B2 * | 10/2007 | Hung | ..................... | C02F 1/484 204/661 |
| 7,491,340 B1 * | 2/2009 | Von Krosigk | ............ | C02F 1/34 210/695 |
| 7,544,323 B1 * | 6/2009 | Von Krosigk | .......... | C02F 1/727 210/748.01 |
| 8,142,550 B2 * | 3/2012 | Audunson | ........... | B01F 3/04985 261/77 |
| 8,403,305 B2 * | 3/2013 | Matsumura | ........... | B01F 3/0446 261/118 |
| 8,992,848 B2 * | 3/2015 | Darragh | ................. | B01J 19/087 204/164 |
| 10,046,292 B1 * | 8/2018 | Dove | ................ | B01F 15/00136 |
| 2015/0191661 A1 * | 7/2015 | Murray | .................. | B01J 19/087 204/168 |
| 2018/0132507 A1 * | 5/2018 | Siegel | ...................... | A47J 31/40 |
| 2018/0178184 A1 * | 6/2018 | Holland | ................ | B03C 1/0335 |

OTHER PUBLICATIONS

"Flow measurement" Wikipedia published Feb. 6, 2016 accessed at <https://en.wikipedia.org/w/index.php?title=Flow_measurement&oldid=703648925> (Year: 2016).*

"Piston pump" Wikipedia published Feb. 28, 2015 accessed at <https://en.wikipedia.org/w/index.php?title=Piston_pump&oldid=649194905> (Year: 2015).*

* cited by examiner

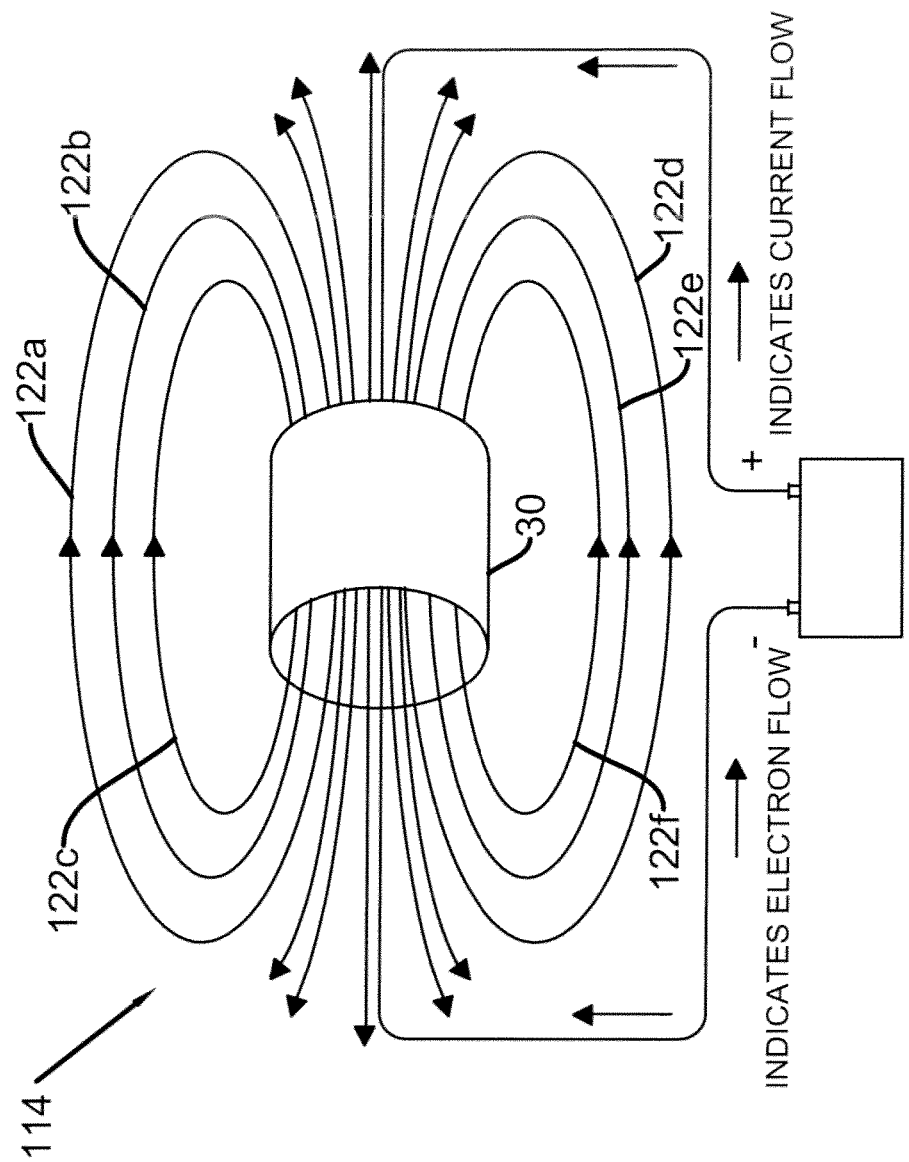

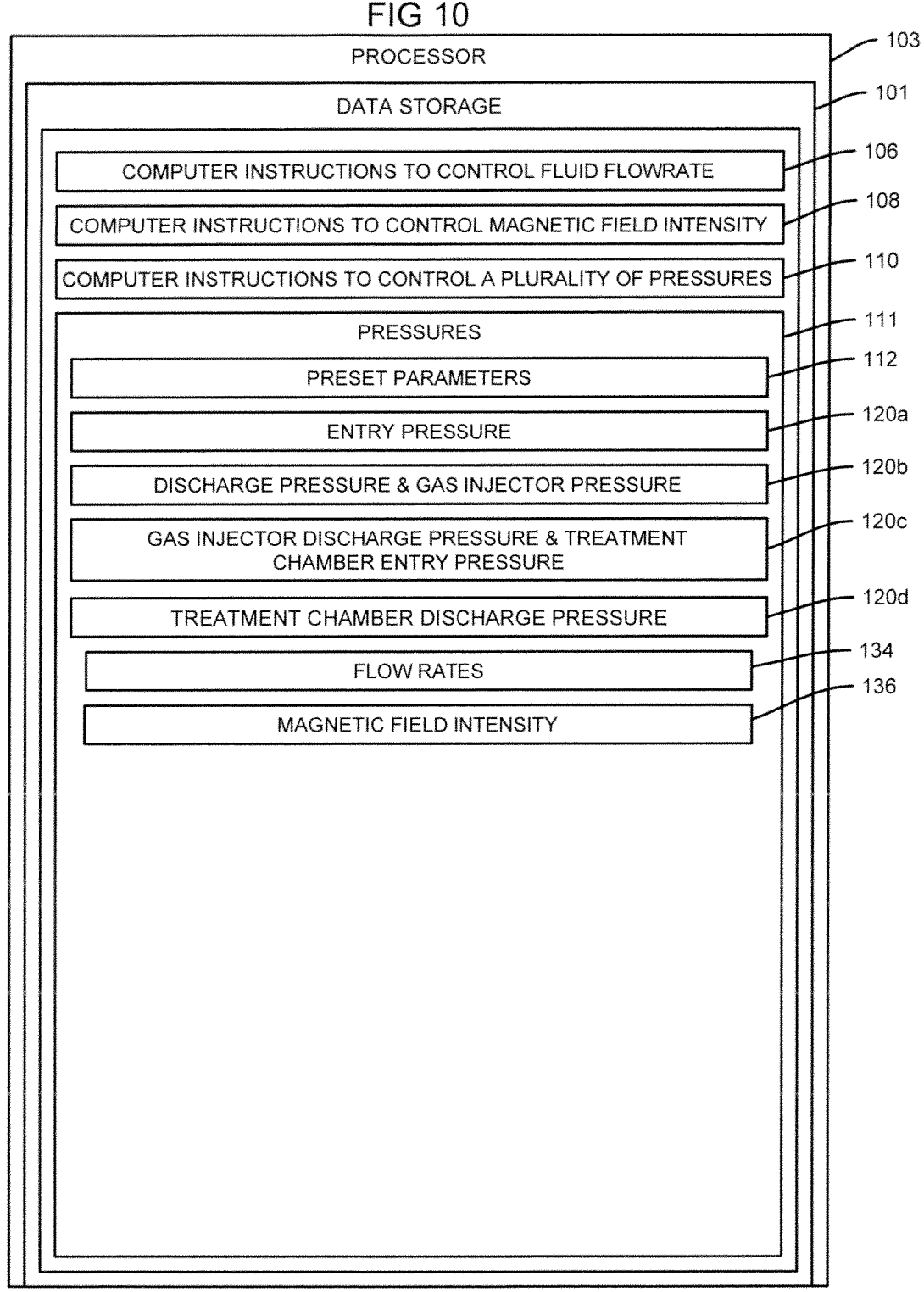

METHOD FOR INCREASING GAS COMPONENTS IN A FLUID

FIELD

The present embodiment generally relates an apparatus for and method of increasing the saturation of a specific gas in a fluid. More specifically, this application relates to increasing oxygen saturation in water.

BACKGROUND

A need exists to improve the saturation level of oxygen in water has an effect in many different industries. The amount of oxygen that can be dissolved into water is related to the temperature and atmospheric pressure of the water. Cold water is able to hold more gas than warmer water and an increase in pressure increases solubility. Without intervention, there is a finite amount of oxygen that can be dissolved into the water according to actuary charts. This finite amount of oxygen may limit the ability to treat wastewater or limit the growth of plants and animals, among other things. Many benefits may be seen by the dispersion of oxygen into water. The same general principles may apply in other industries in relation to other types of gases and fluids.

The present embodiments meet these needs.

BRIEF DESCRIPTION OF THE DRAWINGS

The detailed description will be better understood in conjunction with the accompanying drawings as follows:

FIG. 9 depicts a diagram of the magnetic flux according to one or more embodiments.

FIG. 10 depicts a diagram of the data storage according to one or more embodiments.

Figure 1:
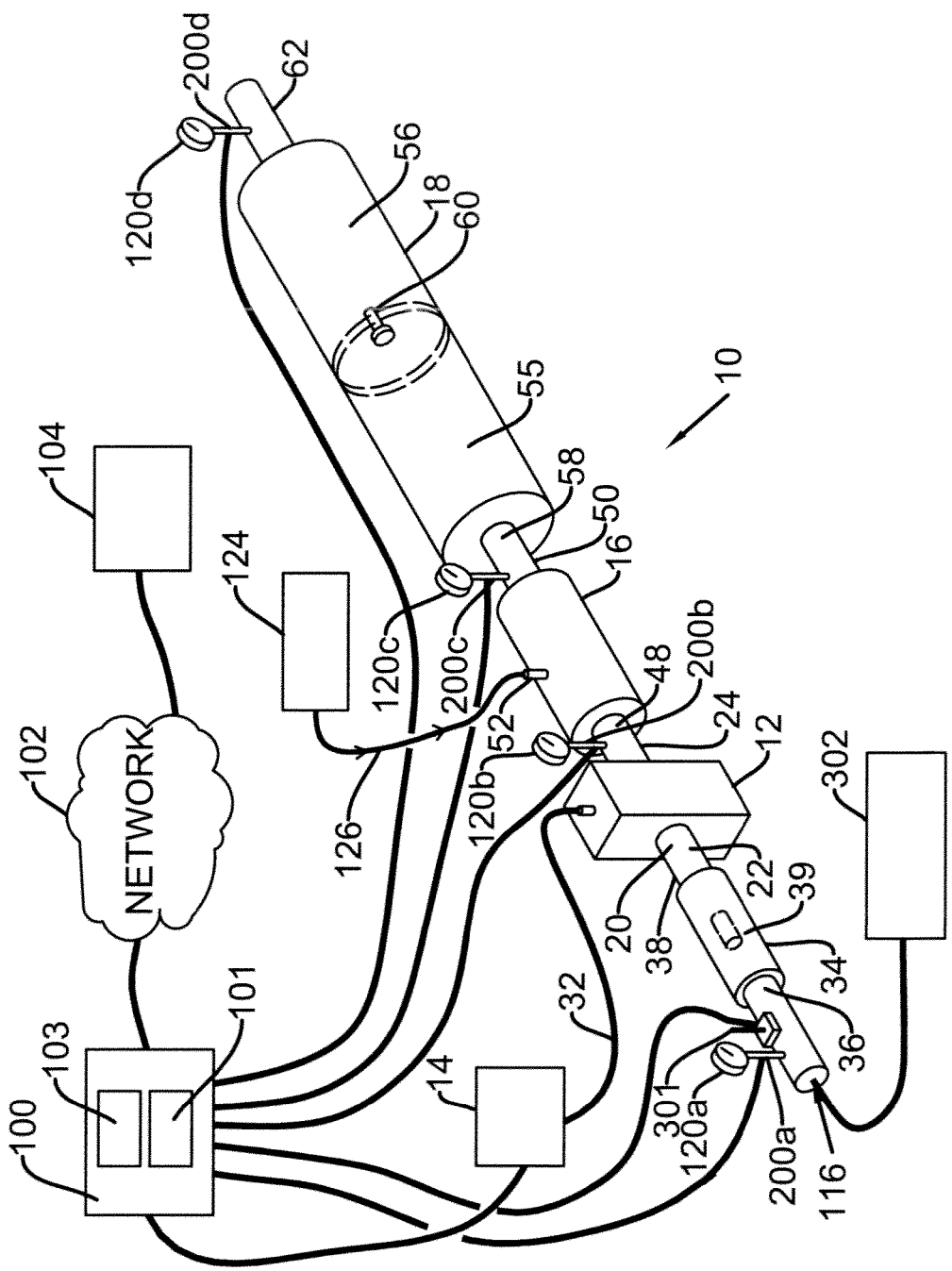
FIG. 1 depicts a schematic view of an apparatus 10 for increasing a gas component in a fluid according to one or more embodiments.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The invention relates to apparatus for increasing gas components in a fluid using a controller connected to a network and a client device for remote control of fluid flow rates, magnet field intensity, and pressure of fluid based on preset parameters stored in the controller.

A conductive wire is coiled around a magnet fluid treatment device forming an "antenna" that generates a bidirectional magnetic flux to magnetically treat fluid in the conduit at an entry pressure.

A variable frequency generator energizes the antennae using from 0.01 Hz to 12,500,000 Hz generating magnetic flux lines that pass through the fluid flow conduit.

A gas injector receives fluid at entry pressure, mixes in gas components and lowers entry pressure to a gas injector discharge pressure.

A treatment chamber receives fluid at gas injector discharge pressure and further lowers the gas injector discharge pressure to a treatment chamber pressure causing absorption of increased gas component in the fluid by from 10% to at least 500%.

The invention described herein may be beneficial for use in a number of different areas and industries including but not limited to wastewater treatment: The energy requirements may be reduced for purification of the activated sludge systems commonly used in industrial and municipal wastewater treatment. There may also be a substantial increase in the capacity of existing wastewater infrastructures. An increase in the rate of microbial metabolic activity may be achieved as a result of the lagoon bottom having an abundance of free molecular oxygen. The free molecular oxygen may provide the infrastructure with a significant increase in wastewater treatment capacity and has the potential to reduce the electrical demands of blowers for an equivalent volume of wastewater treated.

The invention described herein may be beneficial for use in a number of different areas and industries including but not limited to aquaculture: The creation of a molecular solution using the apparatus and method described above may reduce the cost to the aquaculture industry by accelerating the growth rate and lowering the food conversion ratio of the particular species raised via the molecular oxygen in the pond.

The invention described herein may be beneficial for use in a number of different areas and industries including but not limited to reverse osmosis: The treated fluid created through the use of the apparatus and method described above may allow reverse osmosis units to function at substantially higher through-put levels. This in turn could result in a reduction in energy costs. This may be beneficial for creating potable water from seawater.

The invention described herein may be beneficial for use in a number of different areas and industries including but not limited to cleaner flue discharge from power generation facilities and refineries. Carbon, nitrogen and/or sulfur are commonly produced in flue gases of power generation facilities. The method and apparatus described above may be used to convert the carbon, nitrogen and/or sulfur to carbonate, nitrate and/or sulfate which can be removed by scrubbing the flue gas with water and later used as fertilizers. This allows for the possibility of cleaner exhaust gases from flue stacks.

The invention described herein may be beneficial for use in a number of different areas and industries including but not limited to improve concrete curing: The cure time for concrete may be accelerated when the water used to mix the concrete is first treated using the apparatus and method described above. The amount of cement that is used to achieve a certain strength of concrete may be reduced while still achieved the desired strength.

The invention described herein may be beneficial for use in a number of different areas and industries.

The invention described herein may be beneficial for use in a number of different areas and industries including but not limited to emulsion breaking application for chemical and oil refining, and de-oiling of oil drilling fluids and drill bit cuttings from subsurface strata.

The invention described herein may be beneficial for use in a number of different areas and industries including but not limited to improved food production, such as dairy, fruits, grains, vegetables, eggs, beef, pork, poultry and fish.

The invention described herein may be beneficial for use in a number of different areas and industries including but not limited to improved flower production.

The invention described herein may be beneficial for use in a number of different areas and industries including but not limited to fluid purification including fluid sterilization that can be achieved when ozone gas is mixed into the fluid being treated.

The invention described herein may be beneficial for use in a number of different areas and industries including but not limited to improved fuels that may provide for superior combustion, mileage increases, improved waste fluid combustion and lower emissions.

The invention described herein may be beneficial for use in a number of different areas and industries including but not limited to remediation of rivers and lakes by re-oxygenation of contaminated water ways and de-nitrification of water ways In embodiments, the apparatus may be used to create a home based system for the delivery of oxygenated water to a household. Potential benefits of oxygenated water include health benefits, inhibiting scaling on fixtures, reduce the use of soaps, benefit the city sewage treatment and eliminate faults involved in septic tank systems by creating an activated sludge system.

In embodiments, the apparatus could also be used for delivering oxygenated water to a municipality, with potential benefits including improved municipal fluid treatment, expanding the capacity of a central wastewater facility without additional capital costs, eliminating odors and noise, reduction in the cost of future infrastructure expansion and a reduction in the amount of solids left after treatment, thereby reducing haul-off and landfill costs.

Any use herein of any terms describing an interaction between elements is not meant to limit the interaction to direct interaction between the subject elements, and may also include indirect interaction between the elements such as through secondary or intermediary structure unless specifically stated otherwise.

The following terms are used herein:

The term "antenna" refers to a conductive wire coiled around a magnet fluid treatment device. The antenna generates a bidirectional flux field. In embodiments, the magnetic field that can be read at 2 milli-gauss at 20 feet in either direction from the antenna in the connected conduit. The field is a bidirectional flux field, that is, for the 2 milli-gauss unit. The beam extends 20 feet in each direction, for a total of 40 feet. In embodiments the field can be read at 100 milli-gauss, and in such embodiments, the field extends at least 6 feet in each direction. The antenna generates a magnetic field having flux lines that pass through the fluid.

The term "client device" refers to a smart phone, a laptop, another computer, a wearable computer or combinations thereof.

The term "controller" refers to either a computer with processor and memory or a programmable logic circuit with memory.

The term "flow meter" refers to a device for measuring the rate of fluid flow into the pre-treatment electrostatic magnetic assembly or into the antenna when no pretreatment is performed.

The term "fluid" refers to fresh water, sea water, water with particulate up to 50%, effluent from chemical processing and wastewater.

The term "fluid flow conduit" refers to a pipe that fits inside the magnetic fluid treatment device encircling the pipe. The pipe can be a polymer, a composite, or combinations thereof.

The term "fluid flow rate" refers to the rate of fluid flow between the pump and the pre-treatment electrostatic magnetic assembly.

The term "gas components" as used herein refers to at least one of: oxygen, ozone, nitrogen, hydrogen, sulfur, carbonates, and carbon monoxide or any other type of gaseous material.

The term "gas injector" refers to a mixing chamber with a fluid outlet and a gas inlet. The gas inlet of the gas injector connects to a source of the gas components, such as a gas generator that produces a continuous supply of oxygen, ozone, nitrogen, hydrogen, sulfur, carbonates, and carbon monoxide or any other type of gaseous material.

The term "steady state magnetic field intensity" refers to the magnetic field in the pre-treatment electrostatic magnetic assembly.

The term "variable state magnetic field intensity" refers the magnetic field of the antenna once the antenna is energized.

The term "network" refers to a local area network, a wide area network, a cellular network, a global communication network, a satellite network or combinations thereof.

The term "preset parameters" refers to stored operational data stored in the memory of the controller or in memory connected to a processor of a client device.

The term "pressure of the fluid" refers to each of the four different pressures, a pre-treatment pressure, an entry pressure, a gas injector discharge pressure, and a treatment chamber pressure. The pressures are each detectable in the apparatus, namely pressure at an inlet before the pre-treatment electrostatic magnetic assembly, pressure at a conduit between the antenna and the gas injector, pressure at a location in the conduit between the gas injector and the treatment chamber, and pressure in a conduit after the treatment chamber.

The term "pre-treatment electrostatic magnetic assembly" refers to a magnet that provides a steady state magnetic flux on the fluid as it passes through the conduit. In embodiments, 1 to 4 magnets can be used.

The term "pump pressure gauge" refers to a gauge, which displays the pressure from a pressure sensor to a user.

The term "remote control" refers to the bidirectional communication of commands to the apparatus and the receipt of signals from the apparatus for providing bidirectional control of the apparatus as it operates or starts up or shuts down. The remote control can include online configuration and reconfiguration of the apparatus as it operates.

The remote control specifically can control electromagnetic field intensity, magnetic field intensity, fluid flow rates, and pressure on the fluid.

The term "variable frequency generator" refers to a generator that transmits a frequency from 0.01 Hz and 12,500,000 Hz to the antenna to activate the antenna. These generators are commercially available units from China, such as those made by Feeltech Dual Chamber Waveform Generator.

The term "sensor" refers to pressure sensors, temperature sensors, surface tension sensors. Each of the sensors communicates with the controller.

The term "silicate based media" refers to beads, rocks, glass or crystal for the creation of eddies or vortexes in the treatment chamber that assists in the dispersion of the gasses into the fluid.

The term "treatment chamber" refers to a device that can have a single chamber or two chambers and an exit to cause pressure on the fluid to be decreased. In the two chamber version, the treatment chamber can have a primary chamber fluidly connected to a secondary chamber, wherein the secondary chamber has the exit. The primary chamber receives the fluid at a first pressure and passes the fluid to the secondary chamber, wherein the exit drops the pressure. Fluid at the lower pressure then flows to an outlet of the secondary chamber of the treatment chamber. In the embodiment with a single chamber, the fluid enters at an initial pressure, and then the exit connected to the single chamber causes a pressure drop on the fluid enabling the fluid to exit the single chamber at a lower pressure.

In embodiments, the apparatus can include a plurality of sensors mounted to detect fluid flow in the fluid and pressure in the fluid. The sensors are connected to a control processor communicating with a network to a client device. The client device has a processor and instructions in a computer memory at an injector inlet pressure sensor, an injector outlet pressure sensor, a surface tension sensor, and a discharge pressure sensor.

In embodiments, the apparatus can include a pre-treatment electrostatic magnetic assembly having an inlet, an outlet and at least one permanently magnetized magnet, the inlet receiving fluid at an entry pressure. The magnet is positioned such that fluid travelling through the pre-treatment electrostatic magnetic assembly passes the permanently magnetized magnet.

In embodiments, the apparatus can include a flow meter measuring flow into an inlet of the pre-treatment electrostatic magnetic assembly.

In embodiments, the apparatus can include a centrifugal or piston fluid pump connected to a pump pressure gauge connected to the inlet of the pre-treatment electrostatic magnetic assembly. The pump pressure gauge is further connected to the controller.

In embodiments, the apparatus can include a generator connected to the gas injector for providing oxygen, ozone, nitrogen, hydrogen, sulfur, carbonates, and carbon monoxide or any other type of gaseous material.

In embodiments, the treatment chamber of the apparatus has a primary chamber and a secondary chamber. At least one port with a vortex inducing apparatus is positioned between the first chamber and the second chamber.

In embodiments, the apparatus can include a silicate based media contained within the primary chamber of the treatment chamber.

In embodiments, the silicate based media is contained within the secondary chamber of the treatment chamber.

In embodiments, the gas injector can be a venturi injector.

In embodiments, the apparatus can include at least one port with a vortex inducing apparatus creating a vortex within the treatment chamber and acting to enhance the effect that lowering the pressure causes on the dissolving of gas into the fluid.

In embodiments, the antenna can have a conductive wire, preferably made of copper or aluminum that is wrapped around a ferromagnetic magnet. A person of skill will understand that the conductive wire may be made of other appropriate ferromagnetic materials and may even be rare earth magnets.

In embodiments, the antenna encircles at least a portion of a fluid flow conduit, which has an inlet for allowing fluid to enter the center of the antenna and an outlet through which fluid exits antenna.

In embodiments, the variable frequency generator has a cable, which connects to the antenna to energize the antenna. Once activated, the antenna causes a modification to the physical characteristics of the fluid that passes through it.

In embodiments, it should be noted that the pre-treatment electrostatic magnetic assembly can have an inlet, an outlet and a yet another magnet, that is a second magnet for dual magnetic treatment of the fluid. The outlet of the pre-treatment electrostatic magnetic assembly is in fluid communication with inlet of antenna. The pretreatment magnet is positioned such that fluid travelling through pre-treatment electrostatic magnetic assembly passes this pretreatment magnet.

In other embodiments, the second magnet of the pretreatment unit may be positioned within pre-treatment electrostatic magnetic assembly such that fluid flows around this magnet.

In other embodiments, the second pretreatment magnet may be positioned within pre-treatment electrostatic magnetic assembly such that fluid flows between two pretreatment magnets.

The unusual antenna in combination with the pre-treatment electrostatic magnetic assembly is used to modify the physical characteristic of the fluid.

The physical characteristic modification may be achieved by satisfying any active unshared negative electrons of the fluid that passes through, forming altered and satisfied fluid molecules.

A water molecule with a single oxygen atom and two hydrogen atoms and two unshared electrons can be modified in orientation by the magnetic fields.

The orientation of the hydrogen atoms and oxygen atom may cause gases to form bubbles as they enter the water because the non-charged gas is attracted to itself and does not disperse into the fluid as a molecular solution. Due to the shape of the water molecule and the presence of unshared electrons, there could be an uneven distribution of charge which allows neighboring water molecules to be held together by hydrogen bonds.

In embodiments, the antenna modifies the physical characteristics of water molecules by satisfying the unshared pair of electrons. With the unshared electrons being satisfied, the attraction between adjacent water molecules is reduced and hydrogen bonds are less likely to form. The antenna and pre-treatment electrostatic magnetic assembly reduce the attraction of oxygen atoms of water molecules to hydrogen atoms of other water molecules.

In embodiments the flow path of the fluid may be constricted as the fluid enters mixing chamber. This constriction creates a high-velocity stream, which in turn, results in a decrease in pressure to a second pressure that may create a vacuum.

Gas is then drawn or forced through a gas inlet from a gas source, such as an oxygen generator or nitrogen generator and the gas components are mixed with the fluid. The flow path of the fluid can then increase in diameter as the fluid continues through mixing chamber towards a fluid outlet.

The increase in diameter causes a reduction in fluid velocity before the fluid exits fluid outlet and enters into treatment chamber.

Various types of gas injectors may be used in the apparatus. The gas inlet connected to a gas source enables pressurized gas to be drawn or forced through the gas inlet of the mixing chamber into the mixing chamber.

The pressurized gas mixes with the modified fluid in the mixing chamber to create a stable molecular fluid solution. With the attraction between adjacent water molecules being lower due to the satisfied electrons, increased amounts of gas may be dispersed into the fluid. The pressure of the fluid in apparatus is lowered to a second pressure as it travels through gas injector. The stable molecular fluid solution flows through fluid outlet into the treatment chamber.

In embodiments, the treatment chamber can have an inlet in fluid communication with an outlet of the mixing chamber of gas injector.

In embodiments, an exit can be formed from the treatment chamber, which plays a role in lowering the pressure of the fluid travelling through treatment chamber to a third pressure.

The exit is positioned to create a high-velocity stream which results in the decrease in pressure. In embodiments, multiple ports with a vortex inducing apparatus may be used.

The treatment chamber has a fluid discharge outlet for discharging fluid from apparatus.

In other embodiments, the treatment chamber has a primary and a secondary chamber. Fluid enters the primary chamber and flows into the secondary chamber through a port with a vortex inducing apparatus.

The secondary chamber can have a fluid discharge outlet through which treated fluid is discharged from the apparatus.

The stable molecular fluid solution created in the gas injector flows into the primary chamber.

In embodiments, a silicate based media may be provided within primary chamber for pre-treating of the fluids. The purpose of the pre-treatment is to prepare the molecular fluid to be able to disperse more gas. The silicate based media causes the formation of eddies and vortexes within treatment chamber, which assists in the dispersion of the gases.

The silicate based media may contain silicate beads, rocks, glass or crystals.

After pre-treatment, when silicate based media is present, the stable molecular fluid solution flows through a port with a vortex inducing apparatus into a secondary chamber.

The pressure of the fluid in the apparatus is lowered to a third pressure as fluid travels into a secondary chamber as fluid travelling through the at least one port with a vortex inducing apparatus creates a high-velocity stream, which in turn results in a decrease in pressure.

The fourth pressure is preferably the same as or closes to the atmospheric pressure at the fluid discharge outlet.

In embodiments, the port with a vortex inducing apparatus can create a vortex within the secondary chamber or within both primary chamber and the secondary chamber. A vortex helps to maintain gas injected into fluid in the dispersed state and acts to enhance the effect that lowering the pressure has on the disperse-ability of gases. The secondary chamber may be provided with a silicate based media for the treatment of the fluid travelling through it. Once the fluid has passed through secondary chamber, fluid is discharged from apparatus through fluid discharge outlet.

In embodiments, the fluid discharged through fluid discharge outlet is supersaturated with the gas that is mixed into the fluid as it flows through mixing chamber of the gas injector and then the treatment chamber.

After satisfying the unshared pair of electrons in the fluid, the specific gravity may allow the gas molecules to remain in solution for extended periods of time. This may occur because the gas exists in its molecular form and may be suspended or may sink to the bottom of its containment. Whether the gas is suspended or sinks is dependent upon the molecular weight differential between the fluid and the gas that is used.

As an example, an increased saturation level of oxygen n water occurs because the molecular weight of oxygen (approximately 32 g/mol) is heavier than the molecular weight of water (approximately 18 g/mol).

This increased saturation allows the molecular oxygen ($O_2$) to sink to the bottom of its containment and remain in solution instead of bubbling upwards out of solution. The fluid does not have to be water and that the gas used does not have to be oxygen. The fluid may include but is not limited to oily fluids, water, diesel, gasoline or other propellants. The gas that is injected into the fluid is dependent upon the specific results the user wishes to achieve but should be gases that can enter in their molecular form and remain in solution in their molecular form. Oxygen is generally useful where the apparatus is in use for the treatment of fluids where aerobic microbial growth is beneficial, such as for the treatment of wastewater, or for the growth of plants and other organisms in the fluid. Ozone is generally useful where the apparatus is in use for sanitization purposes.

Turning now to the Figures, FIG. 1 depicts a schematic view of an apparatus 10 for increasing a gas component in a fluid.

The apparatus 10 for increasing a gas component in a fluid has a controller 100 with a data storage 101 and processor in communication with a network 102 for communicating with a client device 104 for remote control of the apparatus 10.

The client device enables bidirectional remote control of fluid flow rate, magnetic field intensity, and a plurality of pressures of the fluid based on preset parameters.

In embodiments, the apparatus includes a plurality of sensors 200a-200d penetrating the fluid flow conduit to detect pressure in the fluid. The sensors 200a-200d are connected to the controller 100, communicating with a network 102 to a client device 104.

The apparatus 10 includes a centrifugal or piston fluid pump 302 is connected to a pump pressure gauge connected to the inlet of a pre-treatment electrostatic magnetic assembly 34 and in communication with the controller 100.

A flow meter 301 is connected to the controller 100. The flow meter is configured for measuring flow into an inlet of the pre-treatment electrostatic magnetic assembly 34 and transmitting the measured flow to the controller 100.

In embodiments, the apparatus has a fluid flow conduit 20 to magnetically treat fluid 116 in the fluid flow conduit 20. The fluid 116 arrives in the fluid flow conduit 20 at an entry pressure 120a.

In embodiments, a pre-treatment electrostatic magnetic assembly 4. The pre-treatment electrostatic magnetic assembly 34 has an inlet 36, an outlet 38 and at least one permanently magnetized magnet 39.

In embodiments the permanently magnetized magnet 39 has magnetic anisotropy and magnetic coercivity with magnetic moments due to upward electrons.

In embodiments, the pre-treatment electrostatic magnetic assembly receives fluid at an entry pressure 120a.

The permanently magnetized magnet 39 is positioned such that fluid 116 travelling through the pre-treatment electrostatic magnetic assembly 34 passes the permanently magnetized magnet 39.

In embodiments, a variable frequency generator 14 is electrically connected to the antennae 12 and in communication with the controller 100.

Fluid 116 from the pre-treatment electrostatic magnetic assembly 34 passes through an inlet 22 past an antenna 12 to an outlet 24 at the discharge pressure 120b.

The apparatus includes a gas injector 16. The gas injector 16 has a fluid inlet 48 for receiving the fluid 116 at gas injector entry pressure 120b, a fluid outlet 50 and a gas inlet 52.

The gas inlet 52 is connected to a gas source 124 providing gas components 126.

In embodiments, the gas source 124 can be a generator connected to the gas injector for providing oxygen, ozone, nitrogen, hydrogen, sulfur, carbonates, and carbon monoxide.

The gas injector 16 lowers the gas injector entry pressure 120b of the fluid 116 to a gas injector discharge pressure 120c.

In embodiments, the apparatus 10 includes a treatment chamber 18. The treatment chamber 18 has a primary chamber 55, a secondary chamber 56, a fluid inlet 58, and at least one port with a vortex inducing apparatus 60.

The at least one port with a vortex inducing apparatus 60 can be a flow controller that induces a mass of whirling fluid, which allows the gas component to enter the fluid.

In embodiments, at least one port with a vortex inducing apparatus may include baffles, blades, or deflectors or any other component used for inducing a mass of whirling fluid.

The at least one port with a vortex inducing apparatus 60 is positioned between the primary chamber 55 and the secondary chamber 56.

Once the fluid has passed through secondary chamber 56, fluid is discharged from apparatus through a fluid discharge outlet 62.

The treatment chamber 18 receives the fluid 116 at the treatment chamber entry pressure 120c and lowers the treatment chamber entry pressure to a treatment chamber discharge pressure 120d.

In embodiments, the apparatus causes absorption of increased gas component 126 in the fluid from 10% to at least 500%.

In embodiments, the discharge pressure 120b from the antenna 12 is in the gas injector entry pressure 120b.

In embodiments, the gas injector discharge pressure 120c is the treatment chamber entry pressure of 120c.

Figure 2:
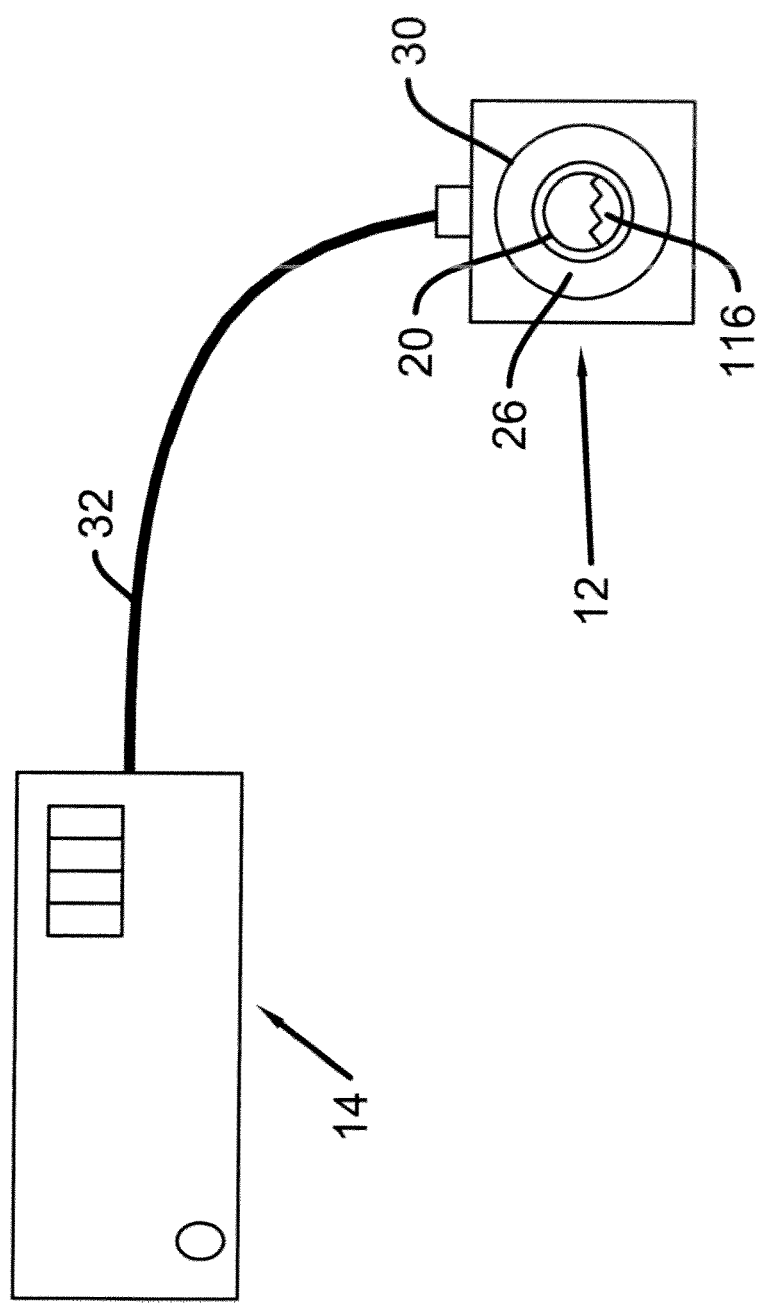
FIG. 2 depicts end elevation view of the antenna connected to the variable frequency generator according to one or more embodiments.

FIG. 2 depicts end elevation view of the antenna connected to the variable frequency generator according to one or more embodiments.

The antenna 12 has a conductive wire 30 coiled around a magnet fluid treatment device 26 generating a bidirectional flux 114.

The magnet fluid treatment device 26 encircles at least a portion of a fluid flow conduit 20 to magnetically treat fluid 116 in the fluid flow conduit. The fluid arrives in the fluid flow conduit 20 at an entry pressure 120a and passes past the antenna 12 to an outlet at the discharge pressure 120b.

The variable frequency generator 14 is electrically connected to the antenna 2 and in communication with the controller.

The variable frequency generator 14 transmits a frequency from 0.01 Hz to 12,500,000 Hz to the antenna 12 to activate the antenna 12 generating a magnetic field having flux lines to pass through the fluid flow conduit 20.

Figure 3:
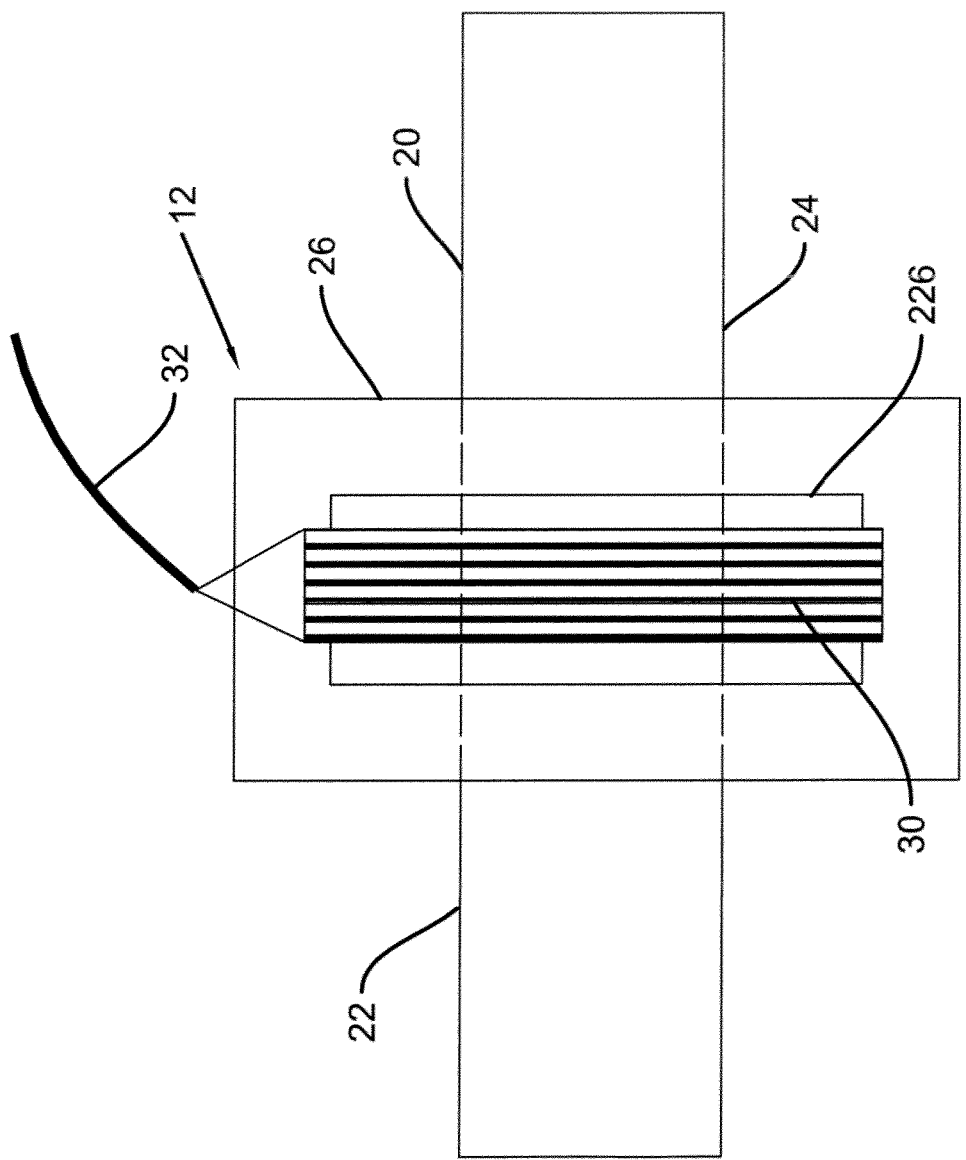
FIG. 3 depicts a section view of the antenna according to one or more embodiments.

FIG. 3 depicts a section view of the antenna according to one or more embodiments.

The antenna 12 is shown with a conductive wire 30 coiled around a magnet fluid treatment device 26. In embodiments, the magnet fluid treatment device includes a magnet 226.

The magnetic fluid treatment device 26 encircles at least a portion of a fluid flow conduit 20 to magnetically treat fluid in the fluid flow conduit 20.

The fluid arrives in the fluid flow conduit 20 through an inlet 22 at an entry pressure 120a and passes past the antenna 12 to an outlet 24 at the discharge pressure 120b.

Figure 4:
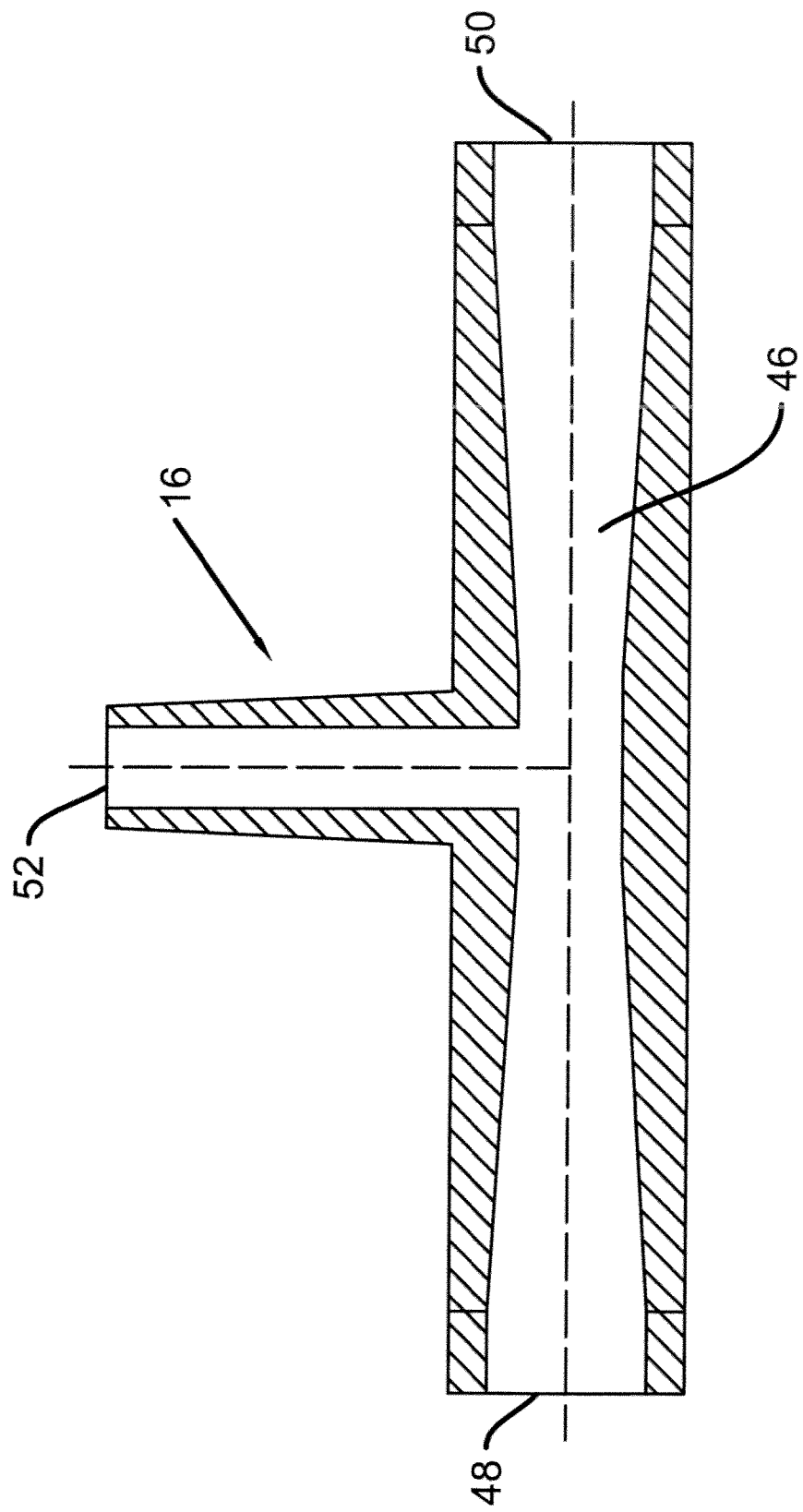
FIG. 4 depicts a section view of a gas injector according to one or more embodiments.

FIG. 4 depicts a section view of a gas injector 16 according to one or more embodiments.

The gas injector 16 has a mixing chamber 46. The mixing chamber has a fluid inlet 48 receiving the fluid at the entry pressure, a fluid outlet 50 and a gas inlet 52.

In embodiments, the gas injector 16 can be a venturi injector.

Figure 5:
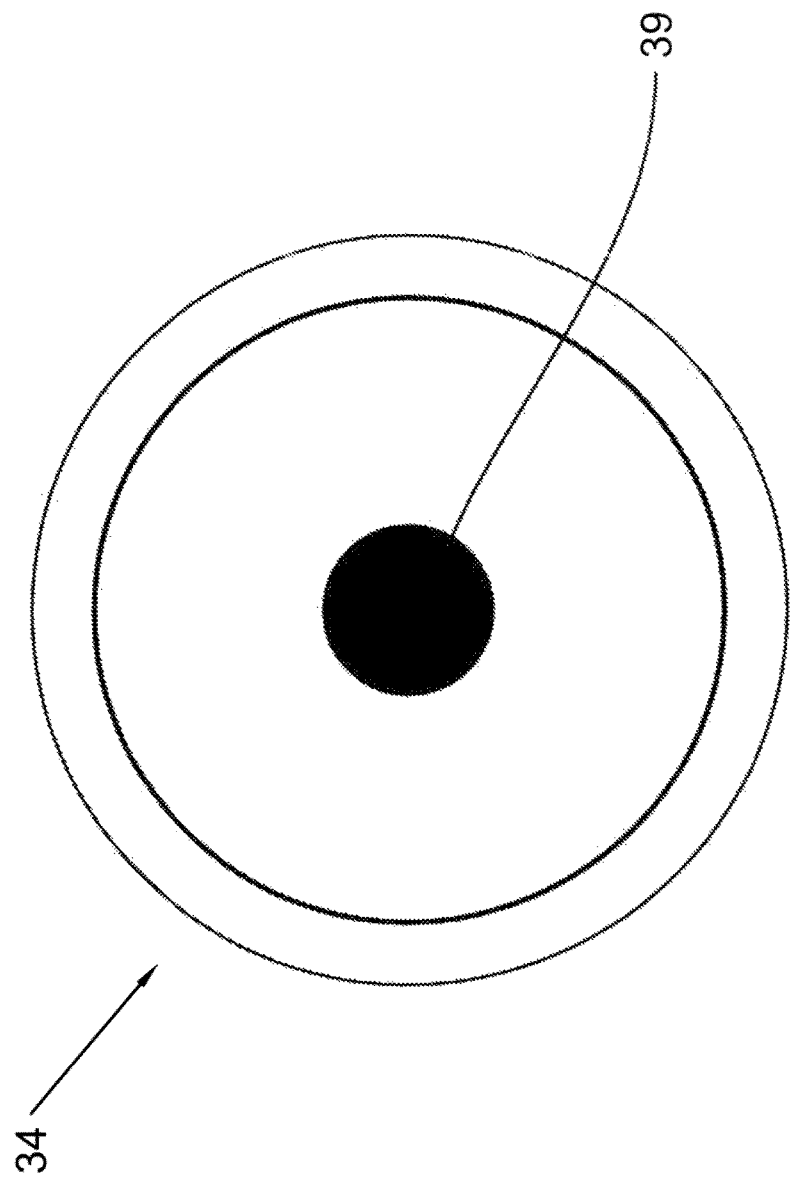
FIG. 5 depicts an end elevation view of a pre-treatment electrostatic magnetic assembly according to one or more embodiments.
Figure 6:
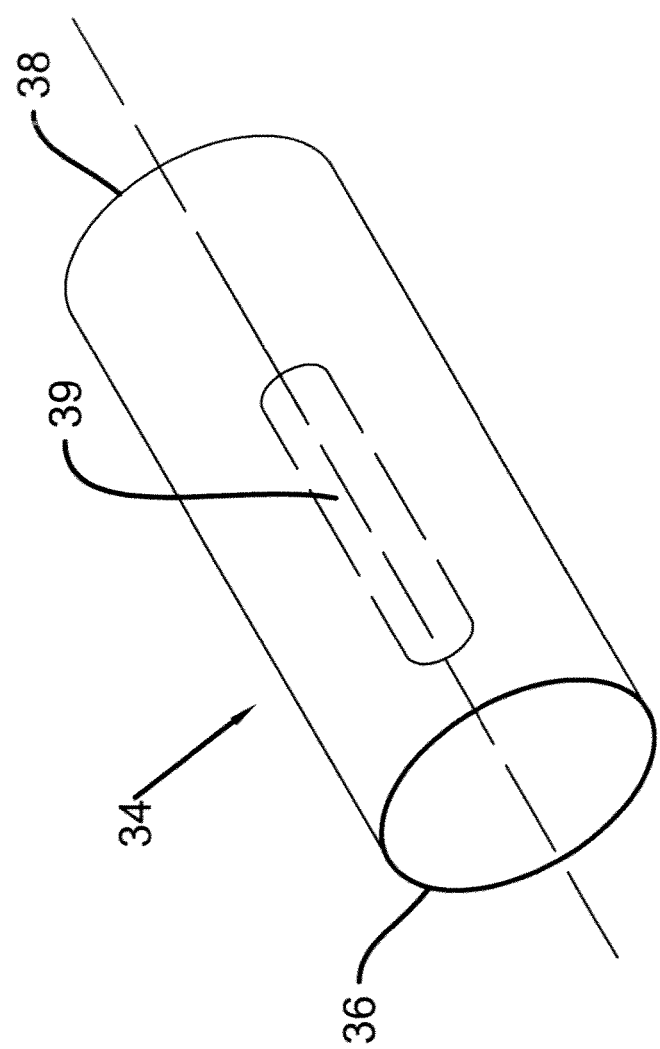
FIG. 6 depicts a section view of the pre-treatment electrostatic magnetic assembly according to one or more embodiments.

FIG. 5 and FIG. 6 depict the pre-treatment electrostatic magnetic assembly 34 according to one or more embodiments.

The pre-treatment electrostatic magnetic assembly 34 has an inlet 36, an outlet 38 and at least one permanently magnetized magnet 39. The inlet receives fluid at the entry pressure 120a.

The permanently magnetized magnet 39 is shown positioned such that fluid travelling through the pre-treatment electrostatic magnetic assembly passes the permanently magnetized magnet 39.

Figure 7:
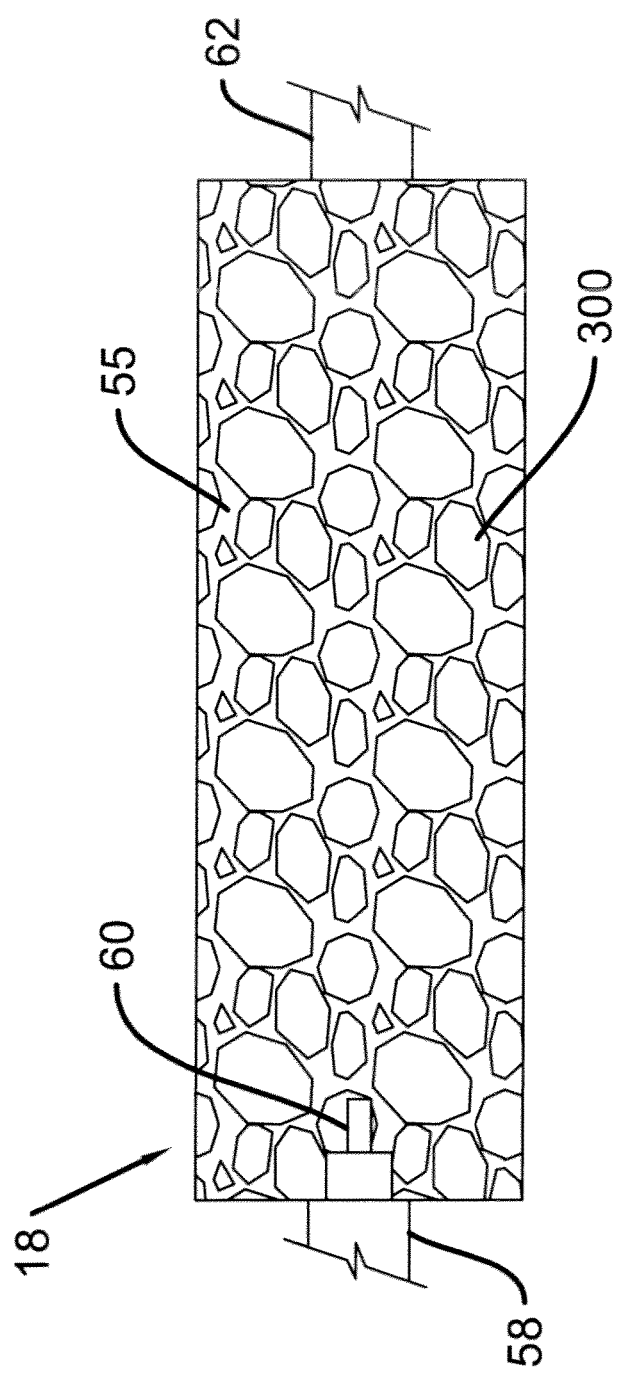
FIG. 7 depicts a section view of a treatment chamber according to one or more embodiments.
Figure 8:
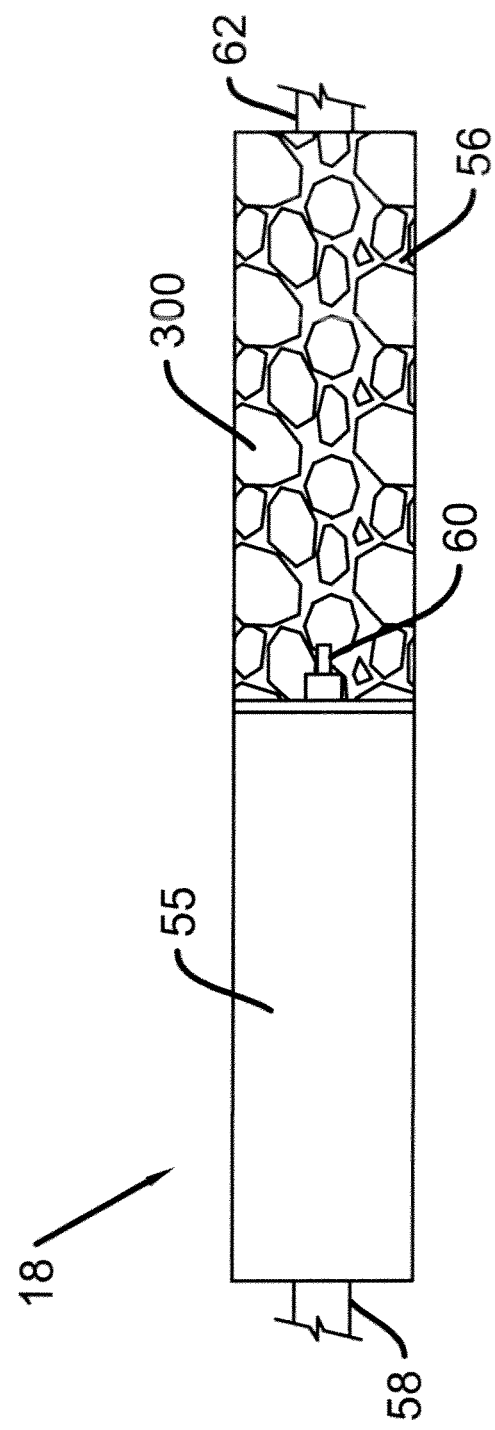
FIG. 8 depicts a section view of a treatment chamber with two chambers according to one or more embodiments.

FIG. 7 and FIG. 8 depict a treatment chamber 18 according to one or more embodiments.

The treatment chamber 18 has a primary chamber 55, a secondary chamber 56, a fluid inlet 58 in fluid communication with the fluid outlet 50 of the mixing chamber 46 of the gas injector and the port with the vortex inducing apparatus 60.

The treatment chamber 18 receives the fluid at the gas injector discharge pressure 128 and lowers the gas injector discharge pressure 120c to a treatment chamber pressure 120d, the apparatus causing absorption of increased gas component 126 in the fluid by from 10% to at least 500%.

In embodiments, a silicate based media 300 can be contained within the primary chamber 55 and secondary chamber 56 of the treatment chamber 18.

Once the fluid has passed through secondary chamber, fluid is discharged from apparatus through fluid discharge outlet 62.

In embodiments, the port with the vortex inducing apparatus 60 can be positioned between the primary chamber 55 and the secondary chamber 56.

The port with the vortex inducing apparatus 60 creates a vortex within the treatment chamber 18 and acts to enhance the effect that lowering the pressure causes on the dissolving of gas into the fluid.

FIG. 9 depicts a diagram of the magnetic flux according to one or more embodiments.

The variable frequency generator is electrically connected to the antenna and in communication with the controller. The antenna with a magnet fluid treatment device generates a bidirectional flux 114. The variable frequency generator transmitting a frequency from 0.01 Hz to 12,500,000 Hz to the antenna to activate the antenna generating a magnetic field having flux lines 122a-122f to pass through the fluid flow conduit.

FIG. 10 depicts a diagram of the data storage 101 according to one or more embodiments.

The data storage 101 is in communication with a processor 103.

In embodiments, the data storage 104 has computer instructions 106 to instruct the processor to control fluid flow rate.

The data storage 101 has computer instructions 108 to instruct the processor to control magnetic field intensity.

The data storage 101 has computer instructions 110 in the data storage 104 to instruct the processor to control a plurality of pressures of the fluid based on preset parameters.

In embodiments, the data storage 101 can include pressures 111, present parameters 112, entry pressure 120a, discharge pressure and gas injector entry pressure 120b, gas injector discharge pressure and treatment chamber entry pressure 120c, the treatment chamber discharge pressure 120d, flow rates 134 and magnetic field intensity 136.

While these embodiments have been described with emphasis on the embodiments, it should be understood that within the scope of the appended claims, the embodiments might be practiced other than as specifically described herein.

What is claimed is:

1. A method for increasing gas components in a fluid, comprising:
   a. communicating between a controller having a processor and data storage in communication with a network and a client device for bidirectional remote control of a fluid flow rate, a magnetic field intensity, and a plurality of pressures of the fluid based on preset parameters;
   b. generating a bidirectional flux using an antenna with a magnet fluid treatment device wherein both the antenna and the magnetic fluid treatment device encircle at least a portion of a fluid flow conduit to magnetically treat the fluid in the fluid flow conduit;
   c. flowing the fluid in the fluid flow conduit at an entry pressure and passing past the antenna to an outlet at a discharge pressure;
   d. transmitting a frequency from 0.01 Hz to 12,500,000 Hz activating the antenna to generating a magnetic field having flux lines to pass through the fluid flow conduit with a variable frequency generator in communication with the controller;
   e. flowing the fluid into a mixing chamber of a gas injector, the mixing chamber receiving the fluid at the gas injector entry pressure, the gas injector comprising a fluid outlet and a gas inlet, the gas inlet being connected to a gas source, the mixing chamber lowering the gas injector entry pressure of the fluid to a gas injector discharge pressure; and
   f. flowing the fluid from the gas injector to a treatment chamber having a primary chamber and a secondary chamber, with a vortex inducing apparatus positioned between the primary chamber and the secondary chamber, the treatment chamber receiving the fluid at a treatment chamber entry pressure and then lowering the treatment chamber entry pressure to a treatment chamber discharge pressure, causing absorption of an increased gas component into the fluid from 10% to 500% and wherein the fluid entering the treatment chamber increases in saturation.

2. The method of claim 1, comprising: the step of using a plurality of sensors to penetrate the fluid flow conduit to detect pressure in a fluid, the plurality of sensors connected to the controller communicating with the network to the client device, the controller configured to instruct the processor to monitor and store the entry pressure, discharge pressure and gas injector entry pressure, gas injector discharge pressure and treatment chamber entry pressure, and the treatment chamber discharge pressure and compare the measured pressures to preset parameters stored in the data storage.

3. The method of claim 1, further comprising using a pre-treatment electrostatic magnetic assembly with a pre-treatment electrostatic magnet having at least one permanently magnetized magnet with magnetic anisotropy and magnetic coercively with magnetic moments due to upward electrons, the pre-treatment electrostatic magnetic assembly receiving the fluid at the entry pressure, passing the fluid at the entry pressure past at least one permanently magnetized magnet to modify fluid surface tension enabling increased absorption of the gas components.

4. The method of claim 1, further comprising using a flow meter connected to the controller to measure flow through a pre-treatment electrostatic magnetic assembly and transmit the measured flow to the controller.

5. The method of claim 1, further comprising using a pump electrically connected to the controller to pump fluid through the fluid flow conduit, the pump consisting of: a centrifugal pump or a piston fluid pump.

6. The method of claim 1, wherein the gas source is a generator connected to the gas injector for providing at least one of oxygen, ozone, nitrogen, hydrogen, sulfur, carbonates, and carbon monoxide.

7. The method of claim 1, further comprising using a silicate based media contained within the primary chamber of the treatment chamber.

8. The method of claim 1, wherein the silicate based media is contained within the secondary chamber of the treatment chamber.

9. The method of claim 1, wherein the gas injector is a Venturi injector.

10. The method of claim 1, wherein the vortex inducing apparatus which creates a vortex within the treatment chamber enhances the effect that lowering the pressure causes on dissolving gas components into the fluid wherein the fluid entering the treatment chamber increases in saturation.

* * * * *